United States Patent [19]

Ohtsuka et al.

[11] 4,130,555

[45] Dec. 19, 1978

[54] PEPTIDE MIXTURES DERIVED FROM COLLAGENOUS MATERIAL OR GELATIN

[75] Inventors: Kazumasa Ohtsuka, Yokohama; Zen Mitsui, Kana; Hajime Wada, Tokyo, all of Japan

[73] Assignee: Nippi Incorporated, Tokyo, Japan

[21] Appl. No.: 830,763

[22] Filed: Sep. 6, 1977

[51] Int. Cl.² ........................... A23J 1/10; C09H 3/00
[52] U.S. Cl. ................................... 260/117; 260/118; 260/123.7; 426/564; 426/590; 426/648; 426/656; 426/657; 424/360
[58] Field of Search .................. 260/117, 118, 123.7

[56] References Cited

U.S. PATENT DOCUMENTS

| | | | |
|---|---|---|---|
| 2,301,242 | 11/1942 | Billaudot | 260/118 |
| 3,445,448 | 5/1969 | McCann | 260/118 |
| 3,514,518 | 5/1970 | Charier-Vadrot | 260/118 X |

*Primary Examiner*—Walter C. Danison
*Attorney, Agent, or Firm*—Hans Berman

[57] ABSTRACT

Peptide mixtures having relatively narrow average molecular weights and characteristic amino acid compositions and a process for preparing the same from a collagenous material or gelatin are disclosed. The peptide mixtures have unique properties and are useful as a water- or moisture-retaining agent for cosmetic articles or foods, a foaming agent for foods, a bitterness-blocking agent for medicines or a nutritional component for soft drinks.

12 Claims, No Drawings

PEPTIDE MIXTURES DERIVED FROM COLLAGENOUS MATERIAL OR GELATIN

This invention relates to a peptides mixture, a process for preparing such mixture from a collagenous material or gelatin and a use thereof. More particularly, this invention relates to two different types of peptide mixtures having a number average molecular weight of from 300-1,200 and a process for preparing such mixtures from a collagenous material or gelatin which comprises hydrolyzing the collagenous material or gelatin, passing the hydrolysate through a column filled with a cation-exchange resin and recovering adsorbed peptide from the column to obtain a peptide mixture having a number average molecular weight of from 300-500 (referred to as the peptide mixture (I) hereinbelow), or a process for preparing such mixture from the collagenous material which comprises hydrolyzing the collagenous material, passing the hydrolysate through a column filled with a cation-exchange resin, recovering unadsorbed hydrolyzed peptide, rehydrolyzing the recovered peptide and then passing it through a column filled with a cation-exchange resin to obtain a peptide mixture having a number average molecular weight of from 500-1,200 (referred to as the peptide mixture (II) hereinbelow).

In one aspect of this invention, two different types of peptide mixtures (I) and (II), each having unique properties or behavior because of its relatively narrow molecular weight distribution and unique amino acid composition, are provided.

In another aspect of this invention, various uses of each type of the peptide mixture are given.

It has been known that oligopeptide which is prepared by partially hydrolyzing some tissue of animals such as skin, bone, tendon and the like with a inorganic acid, an organic acid, an alkali and/or an enzyme, is used as an additive for a cosmetic article, a detergent preparation and the like. Such peptide consisting of natural amino acids has been known to be advantageous as an additive for a cosmetic article because it is less irritating to a human skin when the peptide is directly contacted with the skin. However, it has also been known that a conventional type of peptide does not reveal any positive or advantageous effect to the human skin, even though it causes less skin irritation; namely, such peptide does not have activities improving chapped skin of a person who suffers from dry skin or sweats easily. Thus, the conventional type of peptide could not be expected to improve the skin conditioner or maintain it in good conditions and, more particularly, maintain the moisture of skin surface to a proper level to improve the health and softness of skin.

On the other hand, it has been known that improvement of water-retention properties and integrity of meat or fish product, particularly meat or fish paste is very important to heighten the yield of final product. For that purpose, a phosphate has conventionally been used. However, the use of an excess amount of phosphate gives the final product undesirable sour flavor to lower the quality of flavor. Therefore, it has been desired to develop a method wherein the amount of phosphate used is reduced to a level as small as possible and the reduced water-retention property of the final product is supplemented by another method.

In accordance with this invention, the peptide mixture (I) which has a good water-retention or moisture-retention property can be advantageously used as as additive for cosmetic articles and various foods. The peptide mixture (I) can be added to cosmetic articles such as hair conditioner, lotions, milk lotions, creams, lipsticks or other oily cosmetics to improve their skin conditioning properties.

The peptide mixture (II) prepared according to this invention is useful as a softening agent for a cosmetic cream or lipstick to improve its spreading power and adhering property as well as the property of preventing skin from chapping. In accordance with such properties, the peptide mixture (II) can be incorporated in various cosmetics such as cosmetic creams, lipsticks, mascara, hair conditioners and the like.

The peptide mixture (II) is also useful as a nutritional ingredient for foods or bevarages, particularly for a highly nutritious soft drink. Various nutritious soft drinks have been prepared by blending a protein or its hydrolysate with a palatable fruit juice. However, a protein or its hydrolysate is easily precipitated at a low pH due to fruit juice acidity or other acidic ingredients to make the drink cloudy. Such cloudiness reduces the apparent freshness of the drink. In contrast, the peptide mixture (II) keeps high solubility even under acidic conditions, and therefore, the peptide mixture (II) can be used for a soft drink without forming cloudiness at a concentration sufficient to give a substantially nutritious level to the drink which contains an acidic ingredient.

Further, the peptide mixture (II) is useful as an additive, especially as a foaming agent, for foods. Foams of foods or foodstuff formed with the use of the peptide mixture of this invention are highly uniform and stable. In order to render the foams stable and uniform in size, the peptide mixture (II) according to this invention can be incorporated in dough or batter for sponge cake or bread to give a high quality of product.

Another advantageous use of the peptide mixture (II) of this invention is for blocking the bitterness of medicine. The peptide mixture (II) can block the bitterness of medicine without adversely affecting the pharmacological activities of such medicine when the peptide mixture (II) is added to a preparation containing a pharmacologically active component having bitterness.

The conventional way of blocking bitterness of a medicine is by adding sugar syrup to a liquid pharmaceutical formulation, blending sugar such as lactose to powdery formulation or coating a tabletted formulation with sugar. However, these methods are not sufficient to completely block bitterness. In contrast, the peptide mixture (II) of this invention is very effective for that purpose as stated above.

Medicines to which this invention may be applied include, for example, caffeine, chlorophenylamine maleate, α-mercaptopropyonylglycine, sedium copper chlorophyllin pancreas preparation, bile component preparation, reserpine, vitamin C, nicotinic amide, tetracycline hydrochloride, chloramphenicol, geranium herb extract, suffron extract, Japanese swertia extract, valerian root extract, peony root extract, pyrabitalum, aminopyrine and the like. The amount of the peptide mixture (II) to be used varies, depending upon the sort and amount of the medicine, but generally the amount required is more than 0.1% by weight based on the medicine used.

The peptide mixtures (I) and (II) of this invention are prepared as follows.

A collagen-containing material or gelatin is used as a raw material as it is or after cutting it into small chips. The material is soaked or dispersed in water. The amount of water used is preferably 2-5 times as much as the volume of the raw material. The mineral acid such as HCl or $H_2SO_4$, or an enzyme is added to water containing the raw material. The mixture is heated to dissolve the material in water by hydrolyzing the collagen or gelatin. The number average molecular weight of the hydrolysate, i.e. a mixture of peptides, is preferably in the range from 400 to 3,000. Such hydrolysate having the preferable average molecular weight may be given by the hydrolysis at 50-90° C. for 3-8 hours with the use of concentrated HCl or $H_2SO_4$ in an amount of from 15-50% by weight based on the material.

On the other hand, in the case of an enzyme hydrolysis, the enzyme may be used in an amount of from 0.3-3.0% by weight based on the material and the hydrolysis may be conducted at 30°-60° C. and pH 4-8 for 1-5 hours to give a desired hydrolysate.

The resulting hydrolysate is passed through a column filled with a cation-exchange resin such as one designated IR-120 B. The solution passed through is stocked for preparation of the peptide mixture (II), while the peptide adsorbed on the cation-exchange resin is eluted with weakly alkaline solution such as 2N aqueous ammonia to recover the peptide mixture (I) having a number average molecular weight of from 300-500.

It is found that the peptide mixture (I) is rich in hydroxylysine, lysine, arginine and glycine which are the main constituents of the amorphus portion of collagen, while it is relatively poor in proline and hydroxyproline which are the main amino acids constituting collagen or gelatin. Further, the peptide mixture (I) has a good moisture or water-retention property. The peptide mixture (I) mainly comprises 40-60 residues of hydroxylysine plus lysine, 55-70 residues of arginine, 360-390 residues of glycine 50-70 residues of proline and 60-80 residues of hydroxyproline per 1,000 amino acid residues.

For reference, the amino acid compositions of the typical peptide mixture (I) and gelatin are shown in Table 1 below.

Table 1

| Amino Acids | Comparison in Amino Acid Composition | |
|---|---|---|
| | Peptide Mixture (I) | Gelatin |
| tyrosine | — | 1.0 |
| hydroxylysine | 10.8 | 6.8 |
| lysine | 40.2 | 29.5 |
| histidine | 5.8 | 3.3 |
| arginine | 68.7 | 42.6 |
| cystine | — | — |
| aspertic acid | 51.1 | 45.8 |
| threonine | 17.2 | 15.7 |
| serine | 39.3 | 29.3 |
| glutamic acid | 71.2 | 72.6 |
| proline | 56.1 | 137.3 |
| glycine | 381.6 | 316.1 |
| alanine | 125.5 | 110.7 |
| valine | 18.7 | 22.0 |
| methionine | 3.3 | 2.7 |
| isoleucine | 10.4 | 10.8 |
| leucine | 17.9 | 20.6 |
| phenylalanine | 5.5 | 9.6 |
| hydroxyproline | 76.6 | 123.8 |

Remarks:
The figures show the number of amino acid residues per 1,000 residues of amino acids.

On the other hand, the stocked solution passed through the column filled with the cation-exchange resin which generally has a number average molecular weight of from 2,000 to 3,000 is subjected to hydrolysis with the aid of a mineral acid or an enzyme to give a hydrolysate comprising peptides having a number average molecular weight of from 500-1,200. The hydrolysate is again passed through a column filled with a cation-exchange resin to give the peptide mixture (II).

The peptide mixture (II) is rich is proline and hydroxyproline which are the main constituents of crystalline portions of collagen, while it is poor in hydroxylysine, lysine and arginine which are mainly present in amorphus portions of collagen. The unique properties of the peptide mixture (II) are found to be based on the unique amino acid composition as described above.

A mineral acid which may be used in this invention includes a strong mineral acid such as hydrochloric acid or sulfuric acid in the concentrated form.

An enzyme useful in the process of this invention includes any proper protease and, preferably, Proctase ® which is commercially available from Meiji Seika Kaisha, Ltd., Japan.

An ion-exchange resin which may be used in this invention for purification of hydrolysate is cation-exchange resin, for example, the cation-exchange resin commercially available under the trade mark IR-120 B or SP-Sephadex C-50.

This invention will be further illustrated by the following Examples, but they are not to be construed as limiting the scope of this invention.

EXAMPLE 1

Gelatin (500 g) was added to 1 l of water and, after adding 150 g of 35% HCl, the mixture was heated to a temperature of from 70°-75° C. for 5 hours. The hydrolysate was passed through a column filled with the ion-exchange resin IR-45 and the elute was further poured into a column filled with the cation-exchange resin IR-120 B (H-form). The hydrolysate adsorbed on the resin was eluted with the use of 2N aqueous ammonia to give about 100 g of eluate. The eluate was condensed and dried to form powdery peptide mixture.

Analysis indicated that the average molecular weight of the peptide mixture was 450.

EXAMPLE 2

The peptide mixture prepared according to Example 1 was incorporated into a cosmetic cream having the following formula in a proportion of 1% by weight based on the cream.

| Components | Proportion (% by weight) |
|---|---|
| Solid paraffin | 3.0 |
| Stearyl alcohol | 2.0 |
| Lanolin | 6.0 |
| Vaselin | 6.0 |
| Microcrystalline wax | 1.0 |
| Liquid paraffin | 25.0 |
| Glycerine monostearate | 3.0 |
| Polyoxyethylene monostearate | 3.0 |
| Purified water | 44.0 |
| Propylene glycol | 5.0 |
| Fragrance | 0.5 |
| Preservative | proper amount |

The application of the cream formulated above showed a better moisture retention property to skin surface and, at the same time, kept the skin more fresh in comparison with the skin surface to which was applied the above cream of this invention containing no peptide mixture (II).

EXAMPLE 3

| Chunks of mutton (about 5 cm cube) | 100 (parts by weight) |
|---|---|
| Salt | 2.5 |
| Mixed colorant | 0.25 |
| Seasoning | 1.0 |
| Water | 30 |

The chunks of mutton which had been blended with additives above were separated into two portions and subjected to a comparative test. To one portion of the chunks which was for control was added 0.8 parts of mixed phosphate (sodium polyphosphate:sodium pyrophosphate: sodium acid pyrophosphate = 40:40:20). To other portion of the chunks was added a mixture of 0.2 parts of the mixed phosphate above and 0.6 parts of the peptide mixture prepared (I) according to Example 1. After completion of uniform distribution of the additive, each of the chunks was subjected to salt-curing at 5° C. for 3 days and then processed conventionally to form pressed ham. The ham prepared from the control chunks of mutton had 8.2% of free water, while the ham using the peptide mixture (I) had only 1.2% of free water.

EXAMPLE 4

To 2.5 kg of refined hide pieces (containing 20% of collagen) was added 200 g of 35% HCl and the mixture was heated at a temperature of from 70°-75° C. for 5 hours. The resulting hydrolysate was passed through a column filled with the weakly basic ion-exchange resin IR-45 and then a column filled with the cation-exchange resin IR-120 B (H-form) to give about 3 l of an aqueous solution of peptide having a number average molecular weight of 2,500. The enzyme (Protase: comercially available from Meiji Seika Kaisha, Ltd., Japan) was added to the resulting solution is a proportion of 1% by weight based on the collagen used as raw material and subjected to enzymatic reaction at 50° C. and a pH 6.5-8.0 for 1 half hours. The hydrolysate was passed through a column filled with the ion-exchange resin IR-120 B again and the solution was condensed and dried to give 350 g of a peptide mixture as white powder. The peptide mixture had a number average molecular weight of 850. (Peptide mixture (II))

EXAMPLE 5

Gelatin (500 g) was added to 2 l of water and to the resulting mixture was added 0.5% of Proctase based on the weight of gelatin. The mixture was hydrolyzed at 50°-55° C. and a pH of 6-8 for 2 hours to give an aqueous solution of peptide having a number average molecular weight of about 3,000. Then, the peptide aqueous solution was passed through a column filled with SP-Sephadex C-50 to give about 2.5 l of eluate. Then, 100 g of $H_2SO_4$ (98%) was added to the eluate and the mixture was heated at 65° C. for 4 hours to give hydrolysate. The hydrolysate was again passed through a column filled with the weak alkaline ion-exchange resin IR-45 to desalt the hydrolysate and again passes through a column filled with the cation-exchange resin IR-120 B (H-form). The eluate was condensed to dryness to give 280 g of peptide mixture as white powder. The peptide mixture (II) had a number average molecular weight of 1,100.

EXAMPLE 6

A sponge cake was prepared by the following formulation.

| Components | Amount |
|---|---|
| Wheat flour | 500 g |
| Eggs | 500 g |
| Sugar | 500 g |
| Peptide mixture (II) of Example 4 | 50 g |
| Water | 120 - 150 cc |

The above formulation but omitting the peptide mixture was blended to be foamed. The resulting foam in the batter was eliminated during allowing the batter to stand for 10-30 minutes. In contrast, the formulation above containing the peptide mixture retained the foam in good conditions for 50-60 minutes in the foamed batter. Further, the sponge cake prepared from the batter of the above formulation had good taste and mouthfeel similar to those of the conventional sponge cake.

EXAMPLE 7

A nutritious soft drink was prepared by mixing 100 ml of the 3% peptide mixture (II) aqueous solution, 15 g of sugar, 0.05 g of vitamin C and 0.2 ml of orange flavor essence. The resulting drink had no cloudiness and retained refreshness.

EXAMPLE 8

Various bitter medicines were used to determine the bitterness blocking action of the peptide mixture (II) prepared as in Example 5. Various amounts of the peptide mixture (II) were blended with a different medicine and the bitterness blocking action to each of the medicines was determined by organoleptic test with eight skillful panelers. The results are shown in the following Table 2.

Table 2

| Medicines | Not Added | Amount Added 0.05% | 0.1% | 0.5% |
|---|---|---|---|---|
| Chlorophenylamine maleate | ++ | + | ± | — |
| Caffeine | +++ | ++ | + | ± |
| Pyrabitalum | ++ | + | ± | — |
| Aminopyrine | ++ | + | ± | — |
| Sodium Copper Chlorophyllin | + | + | ± | — |
| Japanese swertia extract | ++++ | +++ | ++ | ++ |

—: not bitter
±: slightly bitter
+: bitter
++: very bitter
+++: strongly bitter
++++: extremely bitter

What we claim is:
1. A peptide mixture prepared by hydrolyzing a collagen-containing material or gelatin which has a number average molecular weight of from 300-500 and contains 40-60 hydroxylysine plus lysine residues, 55-70 arginine residues, 360-390 glycine residues 50-70 proline residues and 60-80 hydroxyproline residues per 1,000 amino acid residues; pouring the hydrolysate into a column filled with a cation-exchange resin; eluting the peptide absorbed on the resin with an alkaline solution; and collecting and condensing the eluate.

2. A process according to claim 1 wherein said cation-exchange resin is a strongly acidic cation-exchange resin of sulfonate type.

3. A process according to claim 1 wherein said hydrolyzing step is effected with the use of 15-50% by weight of concentrated HCl or $H_2SO_4$ based on the material at 50°-90° C. for 3-8 hours, or is effected with the use of 0.3-3.0% by weight of an enzyme based on the material at a pH of 4-8 at 30°-60° C. for 1-5 hours.

4. A process according to claim 1 wherein said alkaline solution is aqueous ammonia.

5. A cosmetic additive which comprises the peptide mixture according to claim 1.

6. An additive for improving the quality of foods which comprises the peptide mixture according to claim 1.

7. A process for preparing a peptide mixture which comprises hydrolyzing again the unadsorbed peptide according to claim 1 passing the hydrolysate through a column filled with a cation-exchange resin again and collecting and condensing the eluate.

8. A process according to claim 7 wherein said hydrolyzing steps are effected under the same or different conditions, said conditions being the presence of 15-50% by weight of concentrated HCl or $H_2SO_4$ based on the material at 50°-90° C. for 3-8 hours, or the presence of 0.3-3.0% by weight of an enzyme based on the material at a pH of 4-8 at 30°-60° C. for 1-5 hours.

9. A process according to claim 7 wherein said cation-exchange resin is a strongly acidic cation-exchange resin of sulfonate type.

10. A foaming agent for foods which comprises the peptide mixture prepared according to claim 7.

11. A nutritional component for soft drinks which comprises the peptide mixture prepared according to claim 7.

12. A bitterness blocking agent for bitter medicines which comprises the peptide mixture prepared according to claim 7.

* * * * *

UNITED STATES PATENT AND TRADEMARK OFFICE
CERTIFICATE OF CORRECTION

PATENT NO. : 4,130,555

DATED : December 19, 1978

INVENTOR(S) : Kazumasa Ohtsuka et al.

It is certified that error appears in the above-identified patent and that said Letters Patent are hereby corrected as shown below:

Claims 2, 3, and 4, line 1 of each, change "process" to -- peptide mixture prepared --.

Signed and Sealed this

Sixth Day of March 1979

[SEAL]

Attest:

RUTH C. MASON
Attesting Officer

DONALD W. BANNER
Commissioner of Patents and Trademarks